United States Patent [19]

Kraft et al.

[11] Patent Number: 5,219,553
[45] Date of Patent: Jun. 15, 1993

[54] COMPOSITION OF A N-CARBOXYMETHYLATED TETRAAZACYCLODODECANE CHELATING AGENT, A PARAMAGNETIC METAL AND EXCESS CALCIUM IONS FOR MRI

[75] Inventors: Karl F. Kraft, Sunnyvale; Steven C. Quay, Los Altos Hills; Scott M. Rocklage, Saratoga; Dilip Worah, Menlo Park, all of Calif.

[73] Assignee: Salutar, Inc., Sunnyvale, Calif.

[21] Appl. No.: 743,212

[22] Filed: Aug. 9, 1991

Related U.S. Application Data

[60] Division of Ser. No. 57,709, Jun. 15, 1987, Pat. No. 5,039,512, which is a continuation-in-part of Ser. No. 893,136, Aug. 4, 1986, abandoned, which is a continuation-in-part of Ser. No. 900,930, Aug. 27, 1986, abandoned.

[51] Int. Cl.$^5$ .................. G01N 24/08; A61K 31/555
[52] U.S. Cl. .......................................... 424/9; 424/4; 128/653.4; 436/173; 436/806; 514/184; 514/836; 514/922
[58] Field of Search ............. 424/4, 9; 128/653.4, 128/654; 436/173, 806; 514/184, 836, 922

[56] References Cited

U.S. PATENT DOCUMENTS

| | | | |
|---|---|---|---|
| 4,478,816 | 10/1984 | Ledley et al. | 424/4 |
| 4,647,447 | 3/1987 | Gries et al. | 424/9 |
| 4,730,066 | 3/1988 | White | 556/50 |
| 4,804,529 | 2/1989 | Bardy et al. | 424/9 |
| 4,826,673 | 5/1989 | Dean et al. | 424/9 |
| 5,039,512 | 8/1991 | Kraft et al. | 424/9 |
| 5,078,986 | 1/1992 | Bosworth et al. | 424/9 |
| 5,082,649 | 1/1992 | VanDeripe | 424/9 |

FOREIGN PATENT DOCUMENTS

| | | |
|---|---|---|
| 8188987 | 6/1988 | Australia . |
| 8900052 | 1/1989 | PCT Int'l Appl. . |
| 736432 | 9/1955 | United Kingdom . |

OTHER PUBLICATIONS

Hart, H. USAEC, Orins-12, 118–135 (1956).
Oser et al., Toxicology and Applied Pharmacology 5: 142–162 (1963); "Safety Evaluation Studies of Calcium EDTA".
Nalbandian et al., Ann. NY Acad Sci. (1959), pp. 779–792; "A New Category of Contrast Media: Water-Soluble Radiopaque Polyvalent Chelates".
Shapiro et al., Ann. NY Acad, Sci. 78:756–757 (1959); "Heavy-Metal Chelates and Cesium Salts for Contrast Radiography".
Sapeika, BMJ, Jul. 16, 1955, pp. 167–169; "Radiographic Use of Lead E.D.T.A. In Man".
Bessman, et al., *Medical Annals of the District of Columbia*, 21, 312–315 (1952).
Rubin, et al., *Science*, 117, 659–660 (1953).

*Primary Examiner*—Glennon H. Hollrah
*Assistant Examiner*—Gary E. Hollinden
*Attorney, Agent, or Firm*—Cushman, Darby & Cushman

[57] ABSTRACT

Magnetic resonance imaging contrast media used to affect the relaxation times of atoms in body tissues undergoing NMR diagnosis are disclosed. Such media comprise (1) a paramagnetic, physiologically compatible complex of (a) a chelant consisting of a N-carboxy methylated tetraazacyclododecane, and (b) a paramagnetic ion of a lanthanide element of atomic numbers 59–70, or of a transition metal of atomic numbers 21–29, 42 or 44, or a physiologically compatible salt of such a complex, and (2) a toxicity-reducing amount of labile calcium ions. The labile calcium ions can be derived from a source other than a salt of said chelant, e.g. an inorganic or organic calcium salt. NMR image-enhancing compositions comprising NMR image-enhancing effective amounts of said contrast media and pharmaceutically acceptable diluents are also disclosed.

21 Claims, No Drawings

COMPOSITION OF A N-CARBOXYMETHYLATED TETRAAZACYCLODODECANE CHELATING AGENT, A PARAMAGNETIC METAL AND EXCESS CALCIUM IONS FOR MRI

This is a division of application Ser. No. 07/057,709, filed Jun. 15, 1987, which was a continuation-in-part of U.S. patent application Ser. No. 893,136, filed Aug. 4, 1986, abandoned, and of U.S. patent application Ser. No. 900,930, filed Aug. 27, 1986, abandoned.

BACKGROUND OF THE INVENTION

The present invention relates to improvements in the enhancing of nuclear magnetic resonance (NMR) imaging of animal tissues, especially cardiac and liver tissues.

X-rays have long been used to produce images of animal tissue, e.g., the internal organs of a patient, the patient being positioned between a source of X-rays and a film sensitive to the rays. Where organs interfere with the passage of the rays, the film is less exposed and the resulting developed film is indicative of the state of the organ.

More recently, another imaging technique has been developed, viz. nuclear magnetic resonance. This avoids the harmful effects sometimes attending X-ray exposure. For improved imaging with X-rays, patients have been given enhancers prior to imaging, either orally or parenterally. After a predetermined time interval for distribution of the enhancer through the patient, the image is taken. To obtain a good image it is desirable that the time after the taking of enhancer be kept to a minimum. On the other hand there is a decrease in effectiveness with time, so desirably the decay should be relatively slow so as to provide a substantial time interval during which imaging can be done. The present invention relates to enhancers for NMR imaging.

In the NMR imaging process, protons in the water of the body relax via two mechanisms referred to as $T_1$ and $T_2$. The rate at which the relaxation process occurs may be altered for some water molecules by giving values that contrast with the norm.

Chemicals that enhance NMR images, referred to as contrast agents, are generally paramagnetic in nature. These may be organic free radicals or transition/lanthanide metals which have from one to seven unpaired electrons.

A necessary prerequisite of any ligand that chelates (binds) a metal to form a contrast agent is that it be stable so as to prevent the loss of the metal and its subsequent accumulation in the body. Other considerations include an ability to reversibly bind water, which in turn increases its contrastability and decreases the dose level required. This ability is clearly important since the interaction between any two nuclear spins through space decreases at a rate equal to the reciprocal of the distance raised to the sixth power.

U.S. Pat. No. 4,647,447 discloses use of an NMR image enhancer consisting of the salt of an anion of a complexing acid and a paramagnetic metal ion. A preferred embodiment is the gadolinium chelate of diethylenetriaminepentaacetic acid (Gd DTPA). From the data reported therein these appear to perform well. However, this compound is rapidly excreted by the kidneys, making the timing of the injection extremely critical. Furthermore, there is virtually no uptake by any solid organ, such as the heart, pancreas or liver.

However, while a number of gadolinium contrast agents are known to work well, there remains the possibility that small amounts of free lanthanides are being released, by decomposition of the agent, into the body. Not being a naturally existing metal in the body, little is known about long term effects.

It is accordingly an object of the present invention to provide alternative image enhancers which avoid one or more of the aforementioned disadvantages.

It is another object of the invention to provide an NMR-image enhancer which does not release lanthanides into the body.

SUMMARY OF THE INVENTION

These and other objects and advantages are realized in accordance with one aspect of the present invention pursuant to which there is provided a calcium or magnesium salt of a paramagnetic, physiologically compatible salt of a physiologically compatible chelate complex of an ion of a lanthanide element of atomic numbers 57-70, or of a transition metal of atomic numbers 21-29, 42, or 44.

Advantageously, the salt of the chelate complex is of the formula I or II

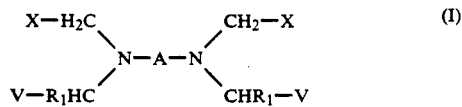

or

wherein

X is —COOY, —PO₃HY or —CONHOY;

Y is a hydrogen atom, a metal ion equivalent or a physiologically biocompatible cation of an inorganic or organic base or amino acid;

A is —CHR₂—CHR₃—, —CH₂—CH₂—(ZCH₂—CH₂)ₘ—,

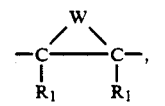

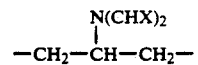

or

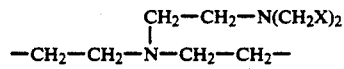

each R₁ is a hydrogen atom or methyl;

R₂ and R₃ together represent a trimethylene group or a tetramethylene group or individually are hydrogen, C₁₋₈-alkyl, phenyl or benzyl, W is —N=N—, —NHCOCH₂— or —NHCS—;

m is the number 1, 2 or 3, z is an oxygen atom, a sulfur atom, NCH₂X, or NCH₂OH₂R₄, R₄ is C₁₋₈-alkyl, V is one of the X groups or is —CH₂OH, or —CONH(CH₂)ₙX, n is a number from 1 to 12;

if $R_1$, $R_2$ and $R_3$ are hydrogen atoms, both V's together are the group

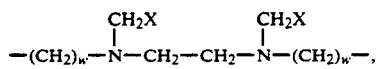

w is a number 1, 2 or 3;

provided that at least two of the substituents Y are metal ion equivalents of an element with an atomic number of 21 to 29, 42, 44 or 57 to 83, and at least one is calcium or magnesium.

Alternatively the calcium or magnesium salt may be a complex of an ion and a ligand, the complexed ion being an ion of a lanthanide element of atomic numbers 57–70, or of a transition metal of atomic numbers 21–29, 42, or 44; and the ligand being that of a calcium or magnesium salt of an organic complexing agent which is acyclic or cyclic and contains organic nitrogen, phosphorus, oxygen or sulfur. In this embodiment, advantageously the complexing agent which forms a (a) an aminopolycarboxylic acid which is nitrilotriacetic acid, N-hydroxyethyl—N,N',N'',N'''-ethylenediaminetriacetic acid, N,N,N',N'',N'''-diethylenetriaminepentaacetic acid or N-hydroxethyliminodiacetic acid;

(b) of the formula

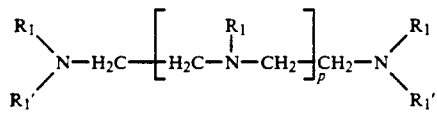

wherein $R_1$ and $R_{12}'$ are identical or different and each is hydrogen or alkyl of 1–4 carbon atoms and p is an integer of 0–4; or (c) an aminopolycarboxylic acid of the formula

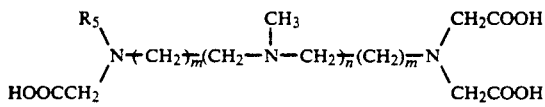

wherein
m is an integer of 1 to 4,
n is an integer of 0 to 2, and
$R_5$ is $C_{4-12}$-alkyl, $C_{4-12}$-alkenyl, $C_{4-12}$-cycloalkyl, $C_{4-12}$-cycloalkenyl, $C_{7-12}$-hydrocarbon aralkyl, $C_{8-12}$-hydrocarbon alkeynl, $C_{6-12}$-hydrocarbon aryl or —$CH_2COOH$.

Such salts are especially useful in the NMR diagnosis of patients to whom they are administered followed by imaging.

The acid moiety of the chelate is advantageously carboxy and phosphono, sulpho being less advantageous. The acid groups are joined to the amino nitrogen by an alkyl, i.e. alkylene, radical of up to 4 carbon atoms. Preferably they are acetic acid radicals, i.e., di-carboxymethylamino radicals, or phosphonic acid radicals as in U.S. Pat. No. 3,738,937.

Preferably there are two amino groups on adjacent carbon atoms and preferably still they are in the trans configuration, e.g., trans-N,N,N',N'-tetracarboxymethyl-1,2-diaminocyclohexane.

If desired, up to two of the carboxylic acid groups may be reacted to form an amide, a lower alkyl ester and/or an anhydride.

The polyvalent paramagnetic metal may be any of those heretofore used in NMR image enhancement, e.g., iron, chromium, cobalt, nickel, neodynium, promethium, samarium, europium, terbium, dysprosium, holmium, erbium, thorium, ytterbium and lutetium Preferably, however, the metal is iron, manganese, or gadolinium.

The metal containing complex is made by adding the cyclic compound to water and adding four mole equivalents of an alkali such as sodium hydroxide or N-methyl-d-glucamine to dissolve the compound. A 1 molar equivalent of manganese chloride or gadolinium chloride is now introduced into the solution. As a result of the chelate formation, the pH of the solution drops to about 5. When manganese chloride is used, rigorous degassing of all water used and compound formation under an inert nitrogen blanket combine to prevent the formation of oxide products during the course of the reaction. The final pH is adjusted to between 5 and 8 and the solution is passed through a 0.2 micron filter for sterilization.

The osmolarity of the resulting solution can be lowered to a physiologically acceptable value by removal of the unnecessary but physiologically acceptable sodium chloride by-product. This can be achieved by crystallization, filtering, dialysis or ion exchange.

The superiority of ring-based contrast agents over other contrast agents which have straight alkane chain backbones, e.g., EDTA (ethylenediaminetetraacetic acid) or DTPA (diethylenetriaminepentaacetic acid) apparently resides in the cyclohexane backbone which imparts more rigidity to the molecule and sterically hinders the coordination of water into the nitrogen-metal bond position. While EDTA divalent metal compounds tend to first break the metal nitrogen bonds by water coordination, the instant system loses the oxygen donors first. This is reflected in the proton nuclear magnetic resonance spectrum of the respective molecules. For example, the manganese salt of trans-N,N,N',N'-tetracarboxymethyl-1,2-diaminocyclohexane (DCTA) has a manganese-nitrogen bond which is considerably more stable than its EDTA analogue. This is reflected in the stability constant (binding ability) towards manganese which is several thousand times better for DCTA than the EDTA chelate. Even though the stability constant of the novel gadolinium complex is approximately the same as the stability constant of Gd DTPA, it is important to note that the novel complex is a tetraacidic ligand while DTPA is pentaacidic. Consequently, inner sphere water coordination is greater and the corresponding relaxation values are considerably better. This improvement allows a decrease in dosage and hence a decreased possible toxicity through degradation and release of free gadolinium.

The addition of calcium or magnesium to the complexes reduces their toxicity. The calcium or magnesium should be present in about 0.1 to 200% and preferably about 10 to 100% based on the moles of paramagnetic polyvalent metal. It can be an inorganic salt such as the chloride or sulfate, but organic salts, e.g., the gluconate, lactate, ascorbate, etc., are preferred.

A calcium or magnesium salt can simply be added to the complex in solution and so administered or the solution can be dried and the dry material later redissolved.

The addition of the calcium or magnesium to the chelate salt surprisingly serves to increase the safety, i.e., to raise the $LD_{50}$ based on the amount of paramagnetic polyvalent metal present.

For example, the MnEDTP chelate without calcium has an $LD_{50}$ of 200 umol/kg, a toxic level. The $LD_{50}$ of the same complex into which 40 mol % of calcium has been incorporated, via calcium gluconate, is in excess of 850 umol/kg, a relatively safe level for human use.

In accordance with another aspect of the invention the acid group is a phosphono moiety. This aspect is applicable even to compounds which are not cyclic, e.g., linear alkylene polyamines such as poly(nitrogen-substituted) phosphonoalkyl alkylenepolyamines, and to compositions not containing a calcium or magnesium salt.

As the poly-phosphono alkylated alkylene polyamine there are preferably employed compounds wherein the alkyl and alkylene radicals each contain up to four carbon atoms. The alkylenepolyamine could be diethylenetriamine, for example, but ethylenediamine is preferred. Advantageously the phosphono groups are joined to the nitrogen atoms through a methyl group, i.e., actually a methylene group. Each phosphono group has two acid moieties so in a compound having four nitrogen atoms there are eight acid moieties available for complexing.

If desired, up to half of those acid moieties can be bound as salts with non-paramagnetic cations, e.g., alkali metal, alkaline earth metal or ammonium salts, or they may be combined as lower alkyl esters, amides and/or anhydrides. The calcium added as the calcium salt has a beneficial effect even beyond that realized if the acid moieties of the polyphosphono alkylated alkylene polyamine are already partially in calcium salt form, for example.

One preferred complexing or chelating agent of this type is N,N,N',N'-tetraphosphonomethylethylenediamine (EDTP) of the structural formula

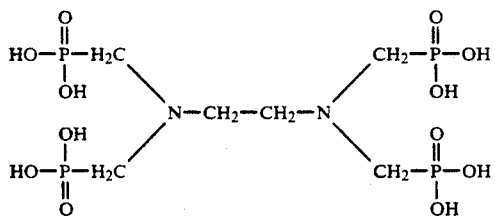

which is commercially available in the form of its sodium salt and free acid.

While lanthanides and particularly gadolinium are highly paramagnetic and useful in accordance with the invention, it is surprising that other less paramagnetic metals perform well, e.g., iron, manganese, copper, cobalt, chromium and nickel.

The complex can be prepared by dissolving a salt of EDTP in water or other solvent and adding a salt of the desired metal, e.g., manganese chloride, in from about half to twice the stoichiometric amount. Additional salts, such as calcium chloride, can be added to tie up additional binding sites in the compound. The solution can then be dialyzed or ion exchanged to remove chloride ions or an alkali such as NaOH can be added to neutralize the chloride ions, the by-product NaCl being removed or left in solution since it is physiologically acceptable.

The Mn-EDTP complex distributes substantially to the following organs: liver, heart, kidneys, spleen, pancreas, bladder, stomach, small and large intestines.

As noted, manganese is the preferred metal, but other polyvalent paramagnetic metals may be used, e.g., iron, chromium, cobalt, nickel, copper, and the like. The preferred lanthanide is gadolinium, but others such as lanthanum, cerium, praseodymium, neodymium, promethium, samarium, europium, terbium, dysprosium, holmium, erbium, thulium, ytterbium and lutetium may also be used.

This invention may be used in conjunction with any magnetic resonance machine currently available and is compatible with any of the current known imaging techniques, e.g., a machine such as that of Siemens AG of Erlanger, Federal Republic of Germany.

Further details of imaging systems are described in the prior art, e.g., "NMR A Primer for Medical Imaging" by Wolf and Popp Slack Book Division (ISBN 0-943432-19-7) and *Scientific American*, May 1982, pages 78–88.

The solution of complex may be sterilized and made up into ampules or may be lyophilized into a powder for dissolution when ready to be used. The solution may be mixed with conventional additives such as saline solution, albumin, buffers and the like. If desired, ampules may be made up containing lyophilized powder of the complex in one compartment and a solution of additives in another separated from the first by a frangible barrier. When ready to use, the barrier is broken and the ampule shaken to form a solution suitable for use.

Immediately prior to actual administration of the contrast agent, the reconstituted solution is further diluted by addition of a suitable diluent such as:

Ringer's Injection, USP
Sodium Chloride Injection, USP
Dextrose Injection, USP (5 percent Dextrose in sterile water)
Dextrose Sodium Chloride Injection, USP (5 percent Dextrose in Sodium Chloride)
Lactated Ringer's Injection, USP
Protein Hydrolysate Injection Low Sodium, USP 5 percent 5 percent with Dextrose 5 percent 5 percent with Invert Sugar 10 percent
Water for Injection, USP The manner and dosage of administration and the manner of scanning are substantially the same as in the prior art. With solutions containing about 50 to 500 mmoles of the complex per liter, sufficient solution should be administered orally or parenterally to provide about 1 to 1 00 umols/kg, corresponding to about 1 to 20 mmol for an adult human patient.

For smaller patients or animals, the dosage should be varied accordingly. The particular complex and organ to be imaged will determine the waiting period between administration and imaging. It will generally be at least about 15 minutes but less than about an hour. During the first few hours the complex is execreted by the liver into the bile.

The invention will be further described in the following illustrative examples wherein all parts are by weight unless otherwise expressed.

EXAMPLE I

Synthesis of DCTP (trans-1,2-diaminocyclohexane-N,N,N,N-tetramethylenephosphonic acid hydrate).

28.5 g (0.25 mole) of trans-1,2-diaminocyclohexane and 82 g (1 mole) of phosphorous acid are dissolved in 140 ml of concentrated hydrochloric acid. The solution is heated to reflux (110° C.) and 162 g (2.1 moles) of formalin (40% aqueous solution of formaldehyde) are added over the course of 90 minutes. The temperature drops to 94° C. and the reaction is maintained at this temperature for 5 hours and then allowed to cool to 25° C. overnight. Crystallization is initiated via scratching the walls of the flask. After standing overnight the precipitated product is isolated via filtration and washed with acetone (3×100 ml). The DCTP is recrystallized from a minimum of water, isolated by filtration, washed with acetone and air-dried. 64 g (52% yield) of pure product are obtained.

Characterization of DCTP

The melting point is 228°-232° C. (decomposition) with slight darkening observed above 220° C.

The positive ion mass spectrum shows a parent ion at 491 mass units (theoretical: 491). Elemental analysis for DCTP $H_2O$ ($C_{10}H_{28}N_2O_{13}P_4$; Calculated: C, 23.63; H, 5.55; N, 5.51; P, 24.38. Found: C, 23.87; H, 5.41; N, 5.48; P, 24.49. Water, 3.71% by Karl-Fischer titration.

Spectrophotometric complexation analysis of DCTP with standardized copper chloride yields percentages of 100.1, 100.6 and 101.2 (average 100.6) assuming a molecular weight of DCTP.$H_2O$ of 508.22.

Nuclear Magnetic Resonance Spectra of DCTP

The proton (400.13 MHz), carbon (100.61 MHz) and phosphorous (161.94 HMz) NMR spectra of trans-1,2-diaminocyclohexane-N,N,N,N-tetramethylenephosphonic acid in dimethyl sulfoxide-d6 do not provide structural and peak assignments through standard NMR techniques. Because of the number of overlapping peaks, 2-dimensional 1H-13C chemical shift correlation NMR techniques are required to make unequivocal peak assignments. The 2D NMR results and analysis of a molecular model indicate an axis of symmetry creating two sets of non-equivalent phosphorous atoms and diasterotopic protons on the methylene carbons adjacent to the phosphorous atoms. The four methylene units create two sets of chemically non-equivalent nuclei. The NMR peak assignments are as follows: 13C (ppm relative to TMS): 63.2 (singlet, methine of cyclohexyl), 50.72 (doublet, Jcp=145.7 Hz, methylene set A of phosphonate), 47.10 (doublet, Jcp=140.4 Hz, methylene set B of phosphonate), 23.9 (singlet, beta-methylene of cyclohexyl), 22.9 (singlet, gamma-methylene of cyclohexyl). 1H (ppm relative to TMS): 8.28 (P-OH), 3.55 (methine of cyclohexyl), 3.50, 3.31, 3.27, 2.88 (methylene of phosphonate), 1.72, 1.16 (beta-methylene of cyclohexyl), 2.10, 1.26 (gamma-methylene of cyclohexyl).

31P (ppm relative to $H_3PO_4$): −19.2, −19.8

The NMR results indicate that the DCTP ligand is relatively rigid on the NMR time-scale; in fact no interconversion is observed up to 60° C. This is in contrast to DCTA, the acetic acid analogue, which is rapidly interconverting on the NMR time-scale at 25° C.

EXAMPLE 2

Formation of Calcium Salt of Manganese Complex of DCTA and DCTP a) To 60 ml of degassed water, 1.6 g (0.04 mole) of sodium hydroxide is added. After the alkali is dissolved, 3.6436 g (0.01 mole) of trans-N,N,N',N'-tetracarboxymethyl-1,2 diaminocyclohexane monohydrate (Aldrich Chemical Co., Milwaukee, Wis.) is added to the stirring solution. 1.979 g (0.01 mole) of manganese chloride tetrahydrate is dissolved in 10 ml of degassed water and is added dropwise to the previous solution. After 30 minutes of stirring, 0.1 mole equivalent of calcium chloride is added to the mixture. The pH of the solution is adjusted to 6.5, and water added to bring the final volume to 100 ml, resulting in a final concentration of 100 mM. The clear or faint yellow solution is filtered through a 0.2 micron filter for sterilization.

b) The calcium salt of the maganese complex of trans-1,2-diaminocyclohexane-N,N,N',N'-tetramethylene phosphonic acid (DCTP) is prepared from the product of Example 1 in a manner analogous to (a).

c) Relaxitivities of protons present in water and plasma exposed to the complexes of (a) and (b) (at 10 mHz) (37° C.) in milliseconds:

TABLE 1

| Molar Concentration (moles/liter) | $T_1$ Water | | $T_2$ Water | | $T_1$ Plasma | | $T_2$ Plasma | |
|---|---|---|---|---|---|---|---|---|
| | (a) | (b) | (a) | (b) | (a) | (b) | (a) | (b) |
| $1 \times 10^{-2}$ | 32 | 16 | 22 | 8 | 25 | 15 | 50.5 | 10 |
| $2 \times 10^{-3}$ | 55 | 28 | 43 | 20 | 39 | 34 | 33.3 | 27 |
| $2.5 \times 10^{-3}$ | 95 | 54 | 69 | 36 | 74 | 51 | 16.9 | 45 |
| $1.25 \times 10^{-3}$ | 171 | 88 | 126 | 69 | 121 | 91 | 9.7 | 74 |
| $6.25 \times 10^{-4}$ | 322 | 172 | | | 223 | 142 | | |
| $3.12 \times 10^{-4}$ | 599 | 310 | | | 336 | 212 | | |
| $1.56 \times 10^{-4}$ | 971 | 555 | | | 513 | 269 | | |
| $7.80 \times 10^{-5}$ | 1390 | 987 | | | 765 | 372 | | | d) $LD_{50}$ values for 40 mice with the complex of (a):

TABLE 2

| Dose (mmole/kg) | Sex | Fatalities | Survivors |
|---|---|---|---|
| 1.5 | Male | 0 | 5 |
| 1.5 | Female | 0 | 5 |
| 2.5 | Male | 1 | 4 |
| 2.5 | Female | 0 | 5 |
| 4.5 | Male | 2 | 3 |
| 4.5 | Female | 3 | 2 |
| 5.5 | Male | 4 | 1 |
| 5.5 | Female | 3 | 2 |

The $LD_{50}$ for (a) was determined to be 4.9 mmol/kg with a 95% confidence range between 4.1 and 5.9 mmol/kg. The $LD_{50}$ for (b) is much lower at 0.2 mmol/kg.

e) Organ distribution of (a) and (b) in male rabbits: The rabbits were sacrificed at 69 minutes post injection for (a) and 15 minutes post-injection for (b) and the proton relaxation values measured in milliseconds, in vitro at 10 mHz, for each of the various organs.

TABLE 3

| Tissue | Normal Values | | (a) | | (b) | |
|---|---|---|---|---|---|---|
| | $T_1$ | $T_2$ | $T_1$ | $T_2$ | $T_1$ | $T_2$ |
| Brain | NA | NA | 637 | 82 | 537 | 85 |
| Heart | 504 | 70 | 367 | 518 | 191 | 40 |
| Lung | 595 | 112 | 472 | 71 | 323 | 84 |
| Fat | 171 | 154 | 176 | 113 | 157 | 95 |
| Skeletal Musc | 423 | 47 | 539 | 62 | 395 | 34 |
| Renal Cortex | 338 | 85 | 123 | 42 | 109 | 51 |
| Renal Medulla | 672 | 149 | 232 | 71 | 103 | 47 |
| Liver | 252 | 64 | 182/137 | 28/37 | 82/66 | 27/24 |
| Pancreas | 464 | 86 | 201 | 49 | NA | NA |
| Stomach | 349 | 69 | 226 | 52 | 199 | 42 |
| Small Intest | 352 | 79 | 115 | 46 | 269 | 60 |
| Large Intest | 349 | 77 | 219 | 44 | 248 | 58 |
| Testis | NA | NA | 623 | 123 | 294 | 79 |
| Urine | NA | NA | 17 | 11 | NA | NA |

NA = Not Available

EXAMPLE 3

Formation of Calcium Salt of Gadolinium Complex of DCTA and DCTP a) 18.218 g (0.05 mole) of trans-N,N,N',N'-tetra-carboxymethyl-1,2 diaminocyclohexane is added to 100 ml of water and 8 g (0.2 mole) of sodium hydroxide is added. 18.585 g (0.05 mole) of gadolinium chloride is then added slowly while stirring. The solution is then stirred for an additional 30 minutes A 0.1 molar equivalent of calcium chloride is added at this point and the pH of the solution adjusted to 6.5. The volume of the solution is brought to 200 ml resulting in a final concentration of 250 mM. The solution is sterilized by passing through a 0.2 micron filter.

b) The calcium salt of the gadolinium complex of trans-1,2-diamino-cyclohexane-N,N,N',N'-tetramethylene phosphonic acid is prepared from the product of Example 1 in a manner analogous to (1).

c) Relaxivities of protons present in water and plasma exposed to (a) and (b) at 10 mHz (37° C.) in milliseconds:

TABLE 4

| Molar Concentration (moles/liter) | $T_1$ Water | | $T_2$ Water | | $T_1$ Plasma | | $T_2$ Plasma | |
|---|---|---|---|---|---|---|---|---|
| | (a) | (b) | (a) | (b) | (a) | (b) | (a) | (b) |
| $1 \times 10^{-2}$ | 22 | 15 | 14 | 8 | 25 | 14 | 20 | 7 |
| $5 \times 10^{-3}$ | 29 | 25 | 25 | 17 | 39 | 20 | 30 | 16 |
| $2.5 \times 10^{-3}$ | 55 | 49 | 47 | 35 | 74 | 36 | 59 | 26 |
| $1.25 \times 10^{-3}$ | 104 | 70 | 89 | 65 | 121 | 60 | 103 | 42 |
| $6.25 \times 10^{-4}$ | 183 | 126 | 161 | 114 | 223 | 95 | | |
| $3.12 \times 10^{-4}$ | 367 | 257 | | | 336 | 149 | | |
| $1.56 \times 10^{-4}$ | 562 | 468 | | | 513 | 263 | | |
| $7.80 \times 10^{-5}$ | 983 | 762 | | | 765 | 447 | | | d) For comparison purposes and to highlight the superior performance of the invention, there follows a table of relaxation values for water and plasma using the N-methyl glucamine salt of Gd DTPA:

TABLE 5

| Molar Concentration moles/liter | Water | | Plasma | |
|---|---|---|---|---|
| | $T_1$ | $T_2$ | $T_1$ | $T_2$ |
| $6.25 \times 10^{-3}$ | 40 | 35 | 39 | 31 |
| $3.13 \times 10^{-3}$ | 83 | 76 | 69 | 61 |
| $1.56 \times 10^{-3}$ | 163 | 155 | 134 | 116 |
| $7.81 \times 10^{-4}$ | 309 | | 240 | |
| $3.91 \times 10^{-4}$ | 582 | | 405 | |
| $1.95 \times 10^{-4}$ | 1015 | | 636 | |
| $9.77 \times 10^{-5}$ | | | 877 | |

It is noted that the relaxation times in Table 1 with the novel manganese complexes are approximately the same as the gadolinium salts in Table 5, even though Table 1 employs a metal with two less unpaired electrons and which is naturally occurring in the body. The gadolinium salts of this invention in Table 4 are still superior.

EXAMPLE 4

Preparation of 100 mM manganese EDTP Complex Containing 40 mM Calcium (1) To 300 ml of water containing 0.2 mol of sodium hydroxide, 21.81 g (0.05 mol) of N,N,N',N'-tetraphosphonomethyleneethylenediamine (referred to as EDTP) is added. The mixture is stirred with a magnetic stirrer until a clear solution is obtained. The pH of the resulting solution is approximately 5.8.

(2) 9.90 g (0.05 mol) of manganese chloride tetrahydrate is dissolved in approximately 15 ml of water and added to the stirring mixture. A precipitate is developed which dissolves on further stirring.

(3) 10 ml of 5M solution of sodium hydroxide is added to the stirring mixture to bring the pH to 5.8.

(4) 2.94 g (0.02 mol) of calcium chloride is added to the mixture. A precipitate that develops dissolves after about 15 minutes of stirring, and the pH drops to 5.6.

(5) The pH is brought back to 5.8 with a solution of 5M sodium hydroxide.

(6) The solution is then brought to a final volume of 500 ml resulting in a concentration of 100 mM for the Mn-EDTP complex and 40 mM for calcium.

(7) The solution is now filtered through 0.2 um filters and stored in vials with butyl rubber stoppers.

The solution is then added to water and to human plasma in varying amounts and the relaxivities measured in conventional manner for comparison with those for the gadolinium complex of the 2-N-methylgulcamine salt of diethylenetriaminepentaacetic acid shown in Table 5, supra.

The following results are obtained, low values for both $T_1$ (transverse relaxation mechanism) and $T_2$ (longitudinal relaxation mechanism) being preferred:

TABLE 6

| Relaxivity of the Compound in Water and in Human Plasma in Milliseconds at 10 MHz (37° C.) | | | | |
|---|---|---|---|---|
| Concentration | Water | | Plasma | |
| molar | $T_1$ | $T_2$ | $T_1$ | $T_2$ |
| $1 \times 10^{-2}$ | 31 | 31 | 18 | 13 |
| $5 \times 10^{-3}$ | 41 | 37 | 31 | 24 |
| $2.5 \times 10^{-3}$ | 83 | 74 | 50 | 38 |
| $1.25 \times 10^{-3}$ | 159 | 123 | 85 | 61 |
| $6.25 \times 10^{-4}$ | 298 | | 112 | 87 |
| $3.125 \times 10^{-4}$ | 537 | | 160 | 116 |
| $1.56 \times 10^{-4}$ | 884 | | 253 | 160 |
| $7.81 \times 10^{-5}$ | 1326 | | 353 | |
| $3.91 \times 10^{-5}$ | | | 478 | |
| $1.95 \times 10^{-5}$ | | | 585 | |
| $9.77 \times 10^{-6}$ | | | 653 | |
| $4.88 \times 10^{-6}$ | | | 797 | |

The relaxivity of the Mn-EDTP-Ca is clearly superior to Gd DTPA. This is especially evident in the $T_1$ values in plasma. For example, at a concentration of $9.77 \times 10^{-6}$M, the value for Mn-EDTP-Ca complex is 653 milliseconds; for Gd DTPA at a 10-fold higher concentration ($9.77 \times 10^{-5}$M) it is 877 msec, i.e., still higher.

EXAMPLE 5

Pharmacokinetics of the Compound of Example 4 in a Pure Breed Beagle Dog

Male dogs are injected with the solution of Example 4 and the comparison compound at 350 umol/kg. Blood is drawn at the indicated times. The plasmas are separated and the $T_1$ relaxivities in milliseconds measured.

TABLE 7

| Time, Min. | $T_1$ Mn-EDTP-Ca | $T_1$ Gd DTPA |
|---|---|---|
| Pre-inj | 1102 | 1427 |
| 10 | 90 | 440 |
| 20 | 108 | 444 |
| 30 | 113 | 551 |
| 45 | 153 | 580 |
| 60 | 222 | 687 |
| 90 | 404 | 860 |
| 180 | 777 | 1282 |
| 360 | 968 | |

Plasma clearance of Gd DTPA is much faster than the Mn-EDTP-Ca Complex. By 180 minutes post-injection, most of the Gd DTPA is cleared from the plasma. Mn-EDTP-Ca is not cleared until 360 minutes post-injection. This gives Mn-EDTP-Ca a larger time "window" for imaging.

EXAMPLE 6

Organ Distribution of the Compound of Example 4 in Male Rabbits

The compound is injected into male rabbits at 50 umol/kg. The rabbits are sacrificed at 15 minutes post injection and the $T_1$ relaxivity of internal organs measured in vitro at 5 MHz (milliseconds). The results are as follows:

TABLE 8

| Organ | $T_1$ Mn-EDTP-Ca | $T_1$ normal organs |
|---|---|---|
| Heart | 240 | 482 |
| Lung | 413 | 585 |
| Fat | 161 | 180 |
| Skeletal Muscle | 260 | 411 |
| Renal Coster | 101 | 342 |
| Renal Medulla | 77 | 782 |
| Liver | 43 | 260 |
| Spleen | 200 | 473 |
| Pancreas | 146 | 265 |
| Bladder | 199 | 511 |
| Stomach | 130 | 305 |
| Small Intestine | 155 | 317 |
| Large Intestine | 133 | 328 |

By comparison according to *Amer.J.Roentol.* 143, 1226, the distribution of Gd DTPA in man at 30 minutes post-injection in milliseconds is:

TABLE 9

| Organ | Pre $T_1$ | Post $T_1$ |
|---|---|---|
| Fat | 200 | 185 |
| Muscle | 460 | 335 |
| Liver | 350 | 195 |
| Spleen | 560 | 285 |
| Kidneys | 820 | 205 |

The organ distribution pattern of Mn-EDTP-Ca is substantially different from Gd-DTPA. It enters the hepatobiliary system resulting in a substantial decrease in $T_1$ values of the liver, spleen, pancreas, and small and large intestines. Gd DTPA, being a vascular agent, is mainly cleared by the kidneys and does not substantially interact with the hepatobiliary system. Mn-EDTP-Ca also distributes to the heart. EKG studies indicate that it does not disturb the function of the heart.

EXAMPLE 7

To 10 ml of water containing 5 ml of 1N sodium hydroxide is added 2.0 g (5 mmoles) of 1,4,7,10-tetraazacyclododecane - N, N',N",N"'-tetraacetic acid. 1.3 g (5 mmoles) of GdCl₃ is added and the suspension heated to 50° C. for 2 hours. Calcium chloride (1 mmole) is added and the pH of the solution adjusted with 1N sodium hydroxide to 6.5. The clear solution is filtered through a 0.2 micron filter for sterilization.

EXAMPLE 8

To 100 ml of water containing 10 g (100 mmoles) of N-methylglucamine is added 19.7 g (50 mmoles) of diethylenetriamine-N,N',N",N"'-pentaacetic acid. 13 g (50 moles) of GdCl₃ is added and the slurry stirred for 1 hour at room temperature. Calcium ascorbate (3.9 g, 10 mmoles) is added and the pH adjusted to 6.5 with 1N sodium hydroxide. The clear 500 mM solution is filtered through a 0.2 micron filter for sterilization prior to use.

It will be understood that the specification and examples are illustrative but not limitative of the present invention and that other embodiments within the spirit and scope of the invention will suggest themselves to those skilled in the art.

We claim:

1. A magnetic resonance imaging contrast medium comprising (a) a paramagnetic, physiologically compatible complex of an N-carboxymethylated-tetraazacyclododecane chelant and a paramagnetic ion of a lanthanide element of atomic number 57-70, and (b) a toxicity-reducing amount of labile calcium ions.

2. A contrast medium as recited in claim 1 wherein the toxicity-reducing calcium ions are derived from a source other than a salt of said chelant.

3. A contrast medium as recited in claim 2 wherein the toxicity-reducing calcium ions are derived from an inorganic or organic calcium salt.

4. A magnetic resonance imaging contrast medium comprising (a) a paramagnetic, physiologically compatible salt of a physiologically compatible complex of an N-carboxymethylated-tetraazacyclododecane chelant and a paramagnetic ion of a lanthanide element of atomic number 57-70, and (b) a toxicity-reducing amount of labile calcium ions derived from a source other than a salt of said chelant.

5. A contrast medium as recited in claim 4 wherein the toxicity-reducing calcium ions are derived from an inorganic or organic calcium salt.

6. A contrast medium as recited in claim 5 wherein the paramagnetic salt is the calcium salt of the gadolinium complex 1,4,7,10-tetraazacyclododecane-N,N',N",N"'-tetraacetic acid.

7. A contrast medium as recited in claim 1 wherein said chelant is 1,4,7,10-tetraazacyclododecane-N,N',N",N"'-tetraacetic acid.

8. A contrast medium as recited in claim 1 wherein said lanthanide is gadolinium.

9. A contrast medium as recited in claim 8 wherein said chelant is 1,4,7,10-tetraazacyclododecane-N,N',N",N"'-tetraacetic acid.

10. A contrast medium as recited in claim 4 wherein said chelant is 1,4,7,10-tetraazacyclododecane-N,N',N",N"'-tetraacetic acid.

11. A contrast medium as recited in claim 4 wherein said lanthanide is gadolinium.

12. A contrast medium as recited in claim 11 wherein said chelant is 1,4,7,10-tetraazacyclododecane-N,N',N",N"'-tetraacetic acid.

13. A magnetic resonance image-enhancing composition comprising a magnetic resonance image-enhancing effective amount of a contrast medium as recited in any one of claims 1-12 inclusive, and a pharmaceutically acceptable diluent.

14. In a method of magnetic resonance imaging in which a contrast medium comprising a physiologically compatible paramagnetic complex of an N-carboxymethylated-tetraazacyclododecane chelant and a paramagnetic ion of a lanthanide element of atomic number 57-50 is administered to a subject and a magnetic resonance image of said subject is generated, the improvement comprising the presence within said contrast medium of a toxicity reducing amount of labile calcium ions.

15. A method as recited in claim 14 wherein the toxicity-reducing calcium ions are derived from a source other than a salt of said chelant.

16. A method as recited in claim 15 wherein the toxicity-reducing calcium ions are derived from an inorganic or organic calcium salt.

17. A method as recited in claim 14 wherein said contrast medium comprises (a) a paramagnetic, physiologically compatible salt of a physiologically compatible complex of an N-carboxymethylated-tetraazacyclododecane chelant and a paramagnetic ion of a lanthanide element of atomic number 57-70 and (b) a toxicity-reducing amount of labile calcium ions derived from a source other than a salt of said chelant.

18. A method as recited in claim 17 wherein the toxicity-reducing calcium ions are derived from an inorganic or organic calcium salt.

19. A method as recited in claim 14 wherein said chelant is 1,4,7,10-tetraazacyclododecane-N,N',N'',N'''-tetraacetic acid.

20. A method as recited in claim 14 wherein said lanthanide is gadolinium.

21. A method as recited in claim 19 wherein said lanthanide is gadolinium.

* * * * *